(12) United States Patent
Lin

(10) Patent No.: US 6,978,785 B2
(45) Date of Patent: Dec. 27, 2005

(54) EYE-SURGICAL HOLED TOWEL

(75) Inventor: Pi-Jung Lin, Taipei Hsien (TW)

(73) Assignee: Iniversal Vision Biotechnology Co., Ltd., Taipei ( * ) Notice: Subject to any disclaimer, the term of this patent is extended or adjusted under 35 U.S.C. 154(b) by 114 days.

(21) Appl. No.: 10/822,282

(22) Filed: Apr. 12, 2004

(65) Prior Publication Data

US 2005/0224081 A1  Oct. 13, 2005

(51) Int. Cl.[7] .................................................. A61F 9/00
(52) U.S. Cl. .................... 128/858; 128/849; 602/74; 2/15
(58) Field of Search .................. 128/858, 857, 128/849, 850, 851, 852, 853, 854, 855, 856; 602/54, 55, 56, 57, 58, 59, 74; 2/410, 424, 2/15, 9, 206

(56) References Cited

U.S. PATENT DOCUMENTS

| | | | |
|---|---|---|---|
| 2,432,767 A * | 12/1947 | Klein | 2/206 |
| 3,667,458 A * | 6/1972 | Krebs | 128/853 |
| 3,956,048 A * | 5/1976 | Nordgren | 128/853 |
| 5,213,114 A * | 5/1993 | Bailey, Jr. | 128/849 |
| RE34,512 E * | 1/1994 | Dowdy et al. | 128/853 |
| 5,709,220 A * | 1/1998 | Kellan | 128/849 |
| 6,405,730 B2 * | 6/2002 | Levitt et al. | 128/849 |
| 6,863,071 B2 * | 3/2005 | Annett et al. | 128/849 |
| 6,871,651 B2 * | 3/2005 | Lanier | 128/852 |

* cited by examiner

Primary Examiner—Fadi H. Dahbour

(57) ABSTRACT

An eye-surgical holed towel comprises a transparent PVC holed towel with two holes at a center thereof; a separable paper adhered to a backside of the holed towel; the separable paper having two holes; and an opaque shielding sheet adhered to a front side of the holed towel and between the two holes of the holed towel; and a lower edge of the opaque shielding sheet being adhered upon the holed towel so that the opaque shielding sheet is turnable along the lower edge for shielding one eye of a user; The two holes of the separable paper are at positions corresponding to the two holes of the holed towel. When the separable paper is torn, it can be placed upon the face of a user. The shielding sheet has a gluing section, when the separable paper is torn, it can be adhered to an eye of the user.

8 Claims, 5 Drawing Sheets

EYE-SURGICAL HOLED TOWEL

FIELD OF THE INVENTION

The present invention relates to holed towels; and particular to an eye-surgical holed towel, wherein the holed towel has two holes. An opaque shielding sheet is installed between the two holes. The shielding sheet is turnable so as to shield one eye. In surgery, the adjustment of the shielding sheet is easy and this the shielding sheet can be firmly secured to the holed towel.

BACKGROUND OF THE INVENTION

Referring to FIG. 1, a prior art eye-surgical holed towel 10a is illustrated. The holed towel has only one single hole 111 and is made of opaque non-weaving cloth 11. The prior art is heavy. Then the holed towel covers upon the face. The holed towel will tightly contact the face of the patient so that the holed towel has a shape like the face, see FIG. 2, especially in the nose. Furthermore, the non-weaving cloth is adhered on the nose so as to affect the breath of the patient and thus to affect the emotion of the user. Moreover, since the non-weaving cloth is non-transparent, it is difficult to find whether the holed towel is correctly disposed. Furthermore, the heavy non-weaving cloth will contact the eyes so as to rub or infect the disease to the user.

Referring to FIG. 3, a holed towel 10b has a single one hole 121 and is made of transparent PVC material. A backside of the holed towel has glue layer 122 for adhering to the face of the user, especially, the periphery of the eyes. Since the material is transparent, it can be corrected easily. Further, because it is light, the problems of affecting breathing and difficulty of arrangement of the holed towel as those induced in non-weaving holed towel 10a. The main problem is that only one hole 121 is formed. When the other eye is to be operated, another holed towel 10 is necessary. In the updating process, a friction between the holed towel 10b and eye will occur. Furthermore, when the holed towel 10b is torn, it must sterilize the eyes and peripheries of the eyes. This makes the process tedious.

Referring to FIG. 4, a holed towel 10c is made of opaque non-weaving cloth 13 with two holes 131. A glue layer 13 is adhered to the face of the patient, and particular to the peripheries of eyes. Before surgery, an opaque shielding sheet 133 serves to shield another eye without surgery. This kind of holed towel with two holes 131 have the advantage that it is unnecessary to tear the holed towel 13 when it is desired to operate another eye after one eye has been operated. Thereby, it is unnecessary to sterilize the eyes, but in this prior art, the shielding sheet 13 is not fixed so that the shielding sheet 133 is possible to displace.

Next, before surgery, an absorbent cloth 134 covers upon the holed towel, see FIG. 4. The absorbent cloth 134 has two holes 134a corresponding to the holes 131 and covers upon the shielding sheet 133 of the holed towel 10c. The area of the holed towel is sufficient to cover the two holes 131. In operation, the absorbent cloth 134 serves to absorb undesired objects flowing from the eyes (such as drug liquid, eye liquid, etc.) However, when the absorbent cloth 134 is too wet, the liquid possibly flows to the ears, see FIG. 5 so that the patient feels uneasy.

Moreover, the holed towel is too small to cover an area including the forehead and jaw of the patient. If the holed towel is too large, the air cannot flow successfully, and thus the patient will feel uneasy and breath of the patient is affected.

SUMMARY OF THE INVENTION

Accordingly, the primary object of the present invention is to provide a eye-surgical holed towel, wherein the holed towel has two holes. An opaque shielding sheet is installed between the two holes. The shielding sheet is turnable so as to shield one eye. In surgery, the adjustment of the shielding sheet is easy and is firmly secured to the holed towel.

Another object of the present invention is to provide an eye-surgical holed towel, wherein the holed towel is made of transparent PVC material. The arrangement of the holed towel can be correctly performed. The backside of the holed towel is adhered to the face of the user for preventing shiftness of the holed towel.

A further object of the present invention is to provide an eye-surgical holed towel, wherein the holed towel is light and has a larger area for covering the forehead, jaw, and ears of the user, but without affecting the breathing of the user.

A yet object of the present invention is to provide an eye-surgical holed towel, wherein a guide bag is installed for collecting undesired objects from the eyes in surgery.

To achieve above objects, the present invention provides an eye-surgical holed towel. The eye-surgical holed towel comprises a transparent PVC holed towel with two holes at a center thereof; a separable paper adhered to a backside of the holed towel; the separable paper having two holes; and an opaque shielding sheet adhered to a front side of the holed towel and between the two holes of the holed towel; and a lower edge of the opaque shielding sheet is adhered upon the holed towel so that the opaque shielding sheet is turnable along the lower edge for shielding one eye of a user; The two holes of the separable paper are at positions corresponding to the two holes of the holed towel; when the separable paper is torn, it can be placed upon the face of a user. The shielding sheet has a gluing section, when the separable paper is torn, it can be adhered to an eye of the user.

The various objects and advantages of the present invention will be more readily understood from the following detailed description when read in conjunction with the appended drawing.

DETAILED DESCRIPTION OF THE INVENTION

In order that those skilled in the art can further understand the present invention, a description will be described in the following in details. However, these descriptions and the appended drawings are only used to cause those skilled in the art to understand the objects, features, and characteristics of the present invention, but not to be used to confine the scope and spirit of the present invention defined in the appended claims.

Figure 1:
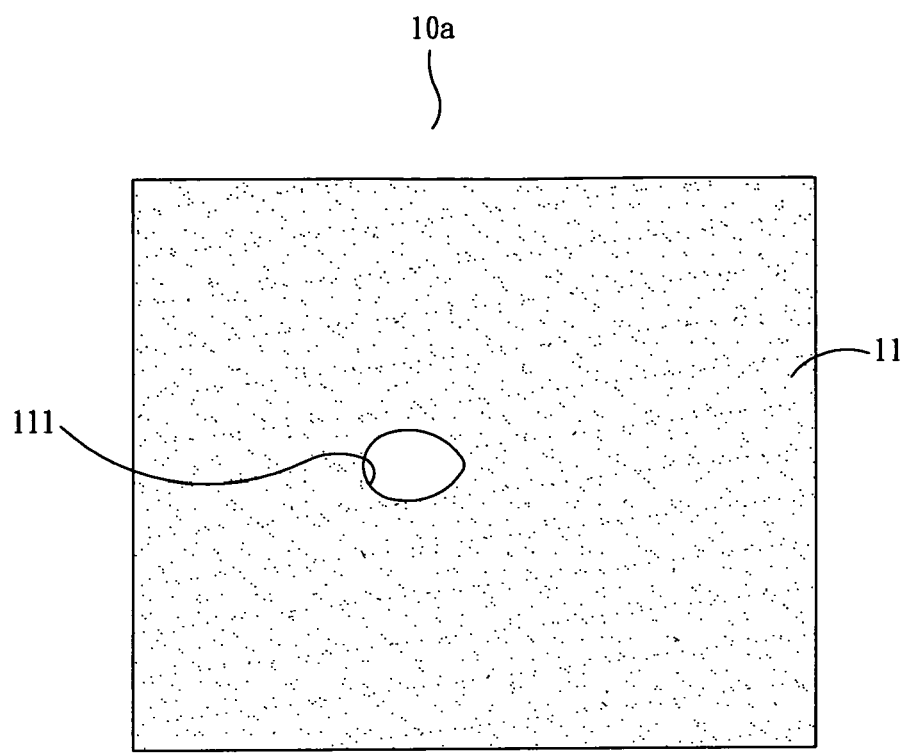
FIG. 1 is a schematic view showing the holed towel of the present invention, which is used in eye-surgery.
Figure 2:
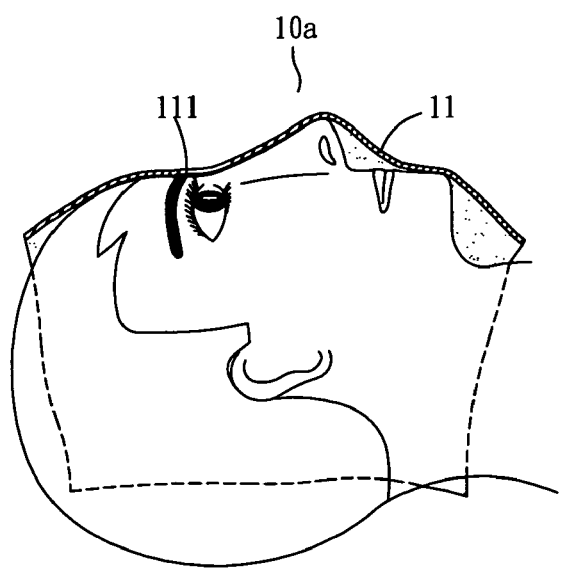
FIG. 2 is a schematic view showing the application of FIG. 1.
Figure 3:
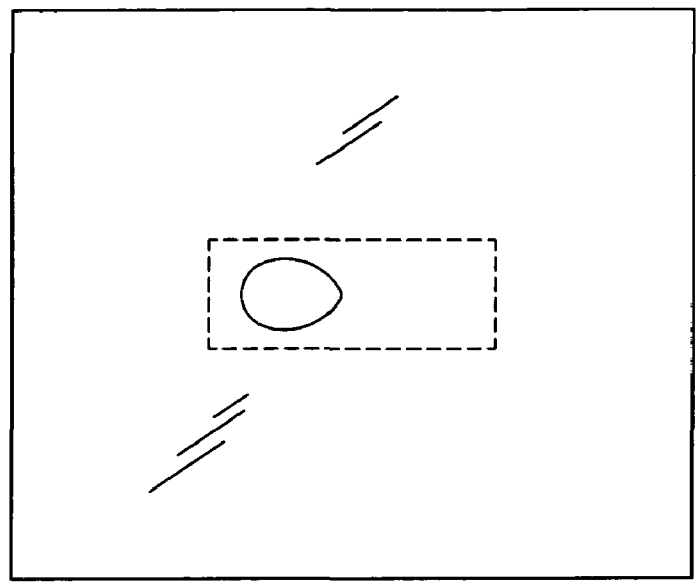
FIG. 3 is a schematic view about the eye-surgical holed towel in another prior art.
Figure 4:
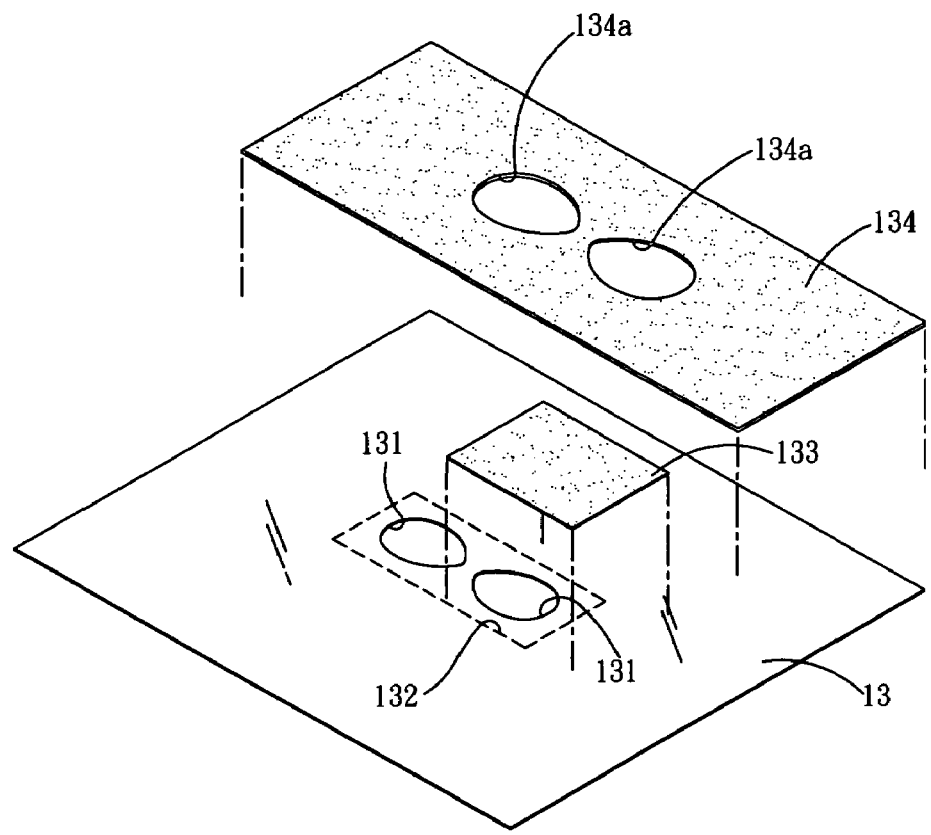
FIG. 4 is a schematic view showing the eye-surgical holed towel in a further prior art.
Figure 5:
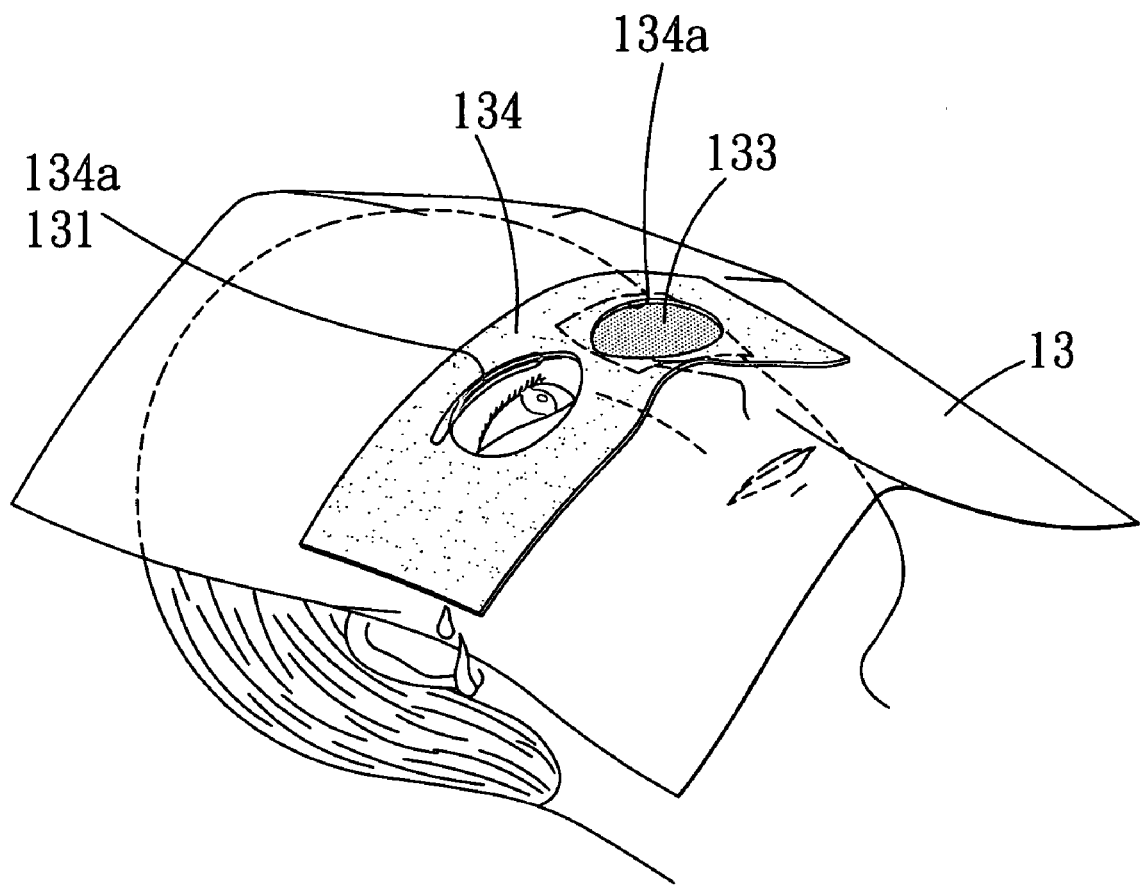
FIG. 5 is a schematic view showing the application of FIG. 4.
Figure 6:
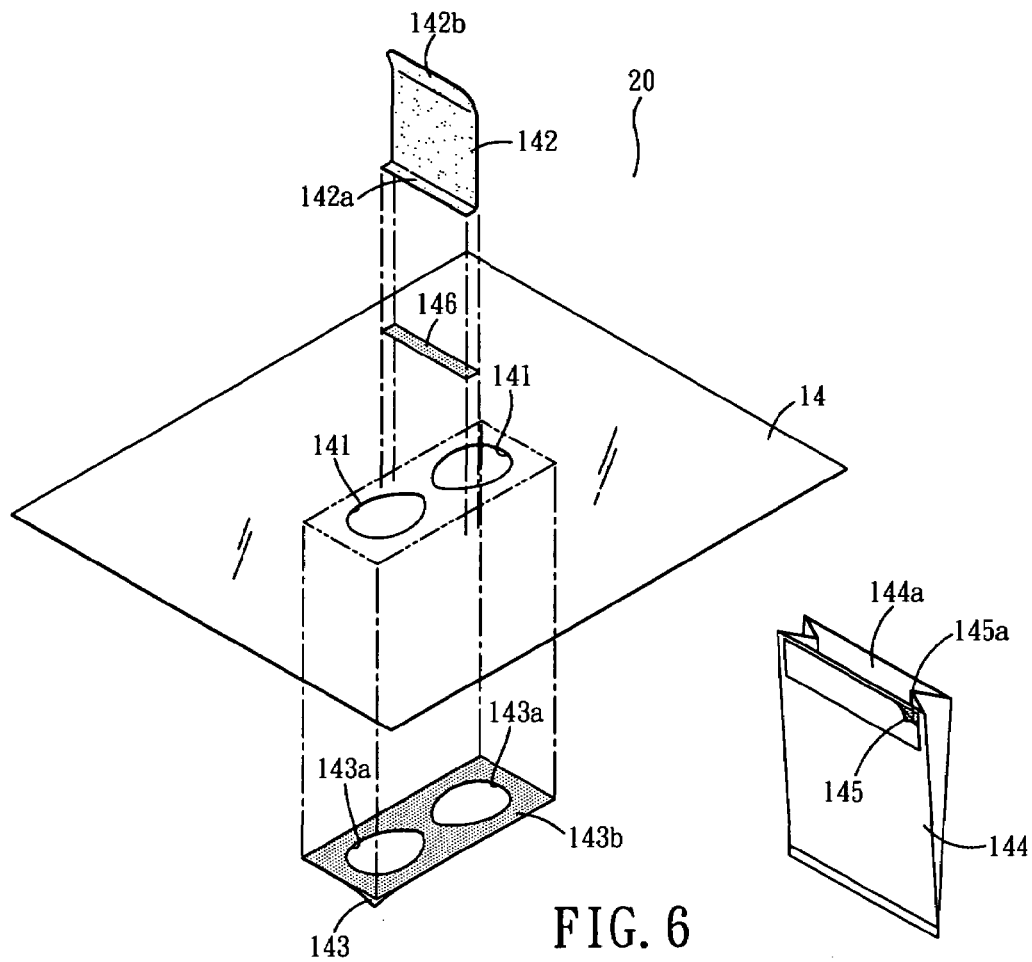
FIG. 6 is an exploded perspective view of the eye-surgical holed towel of the present invention.

The exploded perspective view of the present invention is illustrated in FIG. 6. The eye-surgical holed towel device 20 is illustrated. The holed towel device 20 includes a transparent PVC holed towel 14 having two holes 141; a separable paper 143 installed at a backside of the holed towel 14 and having two holes; and an opaque shielding sheet 142 installed between the two holes of the holed towel 14. Besides, in surgery, the present invention can be used with a guide bag 144.

The coverage of the holed towel 20 includes the forehead, jaw, cheek and ears. In use, it is preferable that the width of the holed towel 14 is larger that the length thereof. For example, the holed towel 14 has a width of 48 cm with a length of 40 cm. Since the holed towel 14 is transparent, the doctor can see the face of the patient so as to correct the pose of the patient. Next, the shielding sheet 142 is made of light non-weaving cloth 14 with a length of 13 cm and a width of 8 cm. The area of the shielding sheet 142 is sufficient to cover a center of the holed towel 14 to one of the holes 141. A lower edge 142a of the shielding sheet 142 is vertically adhered between the two holes 141 of the holed towel 14. Thereby, the shielding sheet 142 is swingable along the lower edge 142a. Furthermore, the tow holes 143a of the separable paper 143 at the backside of the holed towel 14 are aligned to the two holes 141 of the holed towel 14. The separable paper 143 is adhered to the backsides of the holed towel 14 by glue 143b. The area of the separable paper 143 is also 19 cm*8 cm. When the separable paper 143 is torn, the holed towel 14 can be adhered to the face of the patient. The area covering by the glue 143b is exactly adhered to the peripheries of the eyes of the patients. Thereby, the holed towel 14 will not shift or displace.

Moreover, the guide bag 144 is a double layer bag made of transparent PVC material. One end of the bag 144 has an opening 144a and another end thereof is sealed. Two sides of the bag are folded to form a concave section. The guide bag 144 has a length of 22 cm and a width of 15.8 cm. Glue 145a is adhered at one side of the opening 144a and separable paper 145. When the separable paper 145 is torn, the area having the glue 145a can be adhered to one side of one hole 141 and the opening 144a is tightly adhered to a correspondent hole 141 of the holed towel 14.

Figure 7:
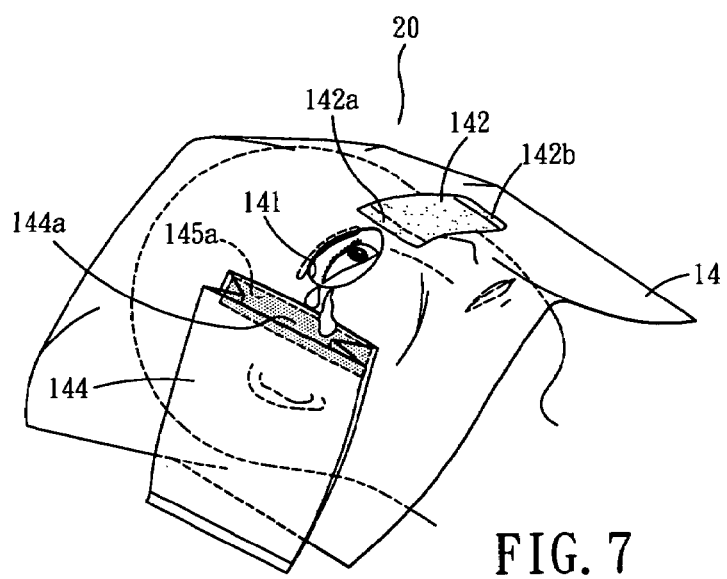
FIG. 7 shows the embodiment of the eye-surgical holed towel of the present invention.

With reference to FIG. 7, a schematic view about the application of the present invention is illustrated. It is shown that the shielding sheet 142 between the two holes 141 of the holed towel 14 will shield one hole 14 (for example, the hole of right eye). When the surgery of the left eye is complete, the surgery of right eye can be performed next. At this time, the shielding sheet 142 originally covering the right eye can be turned to cover the left eye. Since the lower edge 142a of the opaque shielding sheet 142 is adhered to the holed towel 14, it only turns around the lower edge. To make the shielding sheet 142 to be taken easily, a folding line 142b can be formed at another end of the shielding sheet 142. By the slightly upward-inclined area of the shielding sheet 142, the doctor can turn the shielding sheet 142 by fingers.

Moreover, the guide bag 144 is adhered to one side of the hole 141 to be operated, and the opening 144a of the bag covers the hole (a width of the opening is 15 cm). When the patient lies down, the guide bag 44 will be placed correctly (namely, the opening facing upwards and the bottom of the bag facing downward). Thereby, the undesired objects in surgery will be guided into the guide bag 144 through the opening 144a. The guide bag has a preferred collecting function. Sine the guide bag is sufficient to receiving many objects; the user don't worry about any object will flow out of the bag.

Figure 8:
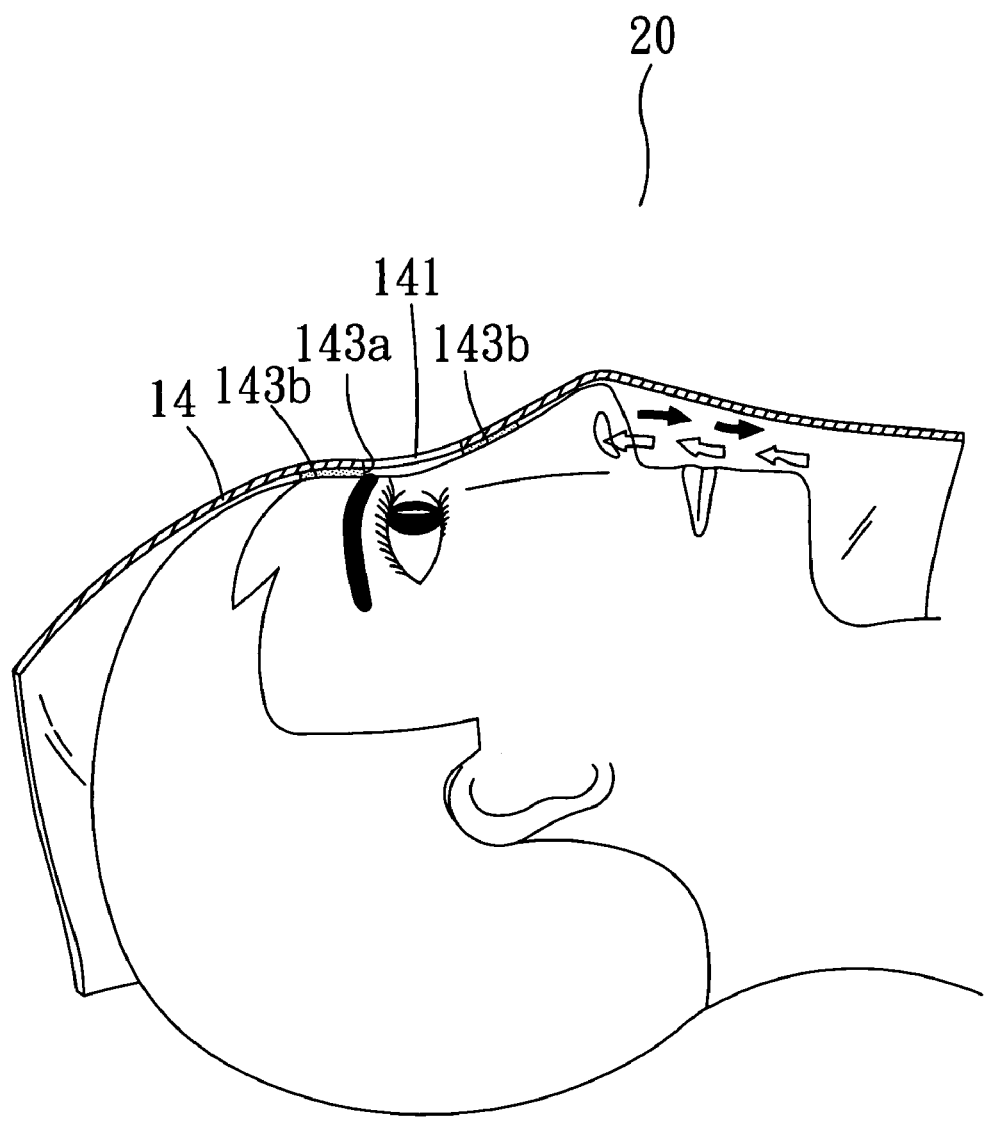
FIG. 8 shows the application of the eye-surgical holed towel of the present invention.

An application of the present invention is illustrated in FIG. 8. It is known from the drawing that when the holed towel 14 covers upon the face of the patient, the upper side thereof is sufficient to cover the forehead of the user, while the lower side thereof is sufficient to cover the jaw of the patient. Two sides of the holed towel 14 covers the ears. Furthermore, the holes 141 and 143b are at positions corresponding to the center of the holed towel. Each hole has an egg shape with a length of 7 cm and width of 4.7 cm. The gap between two holes is 2 cm, which is sufficient to adhere the lower edge 142a of the shielding sheet 142. Since the holed towel 14 is light, the lower portion of the nose will be covered by the holed towel 14. Therefore, the patient can breathe successfully and feel easy.

The present invention is thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An eye-surgical holed towel comprising:
   a transparent PVC holed towel with two holes at a center thereof;
   a separable paper adhered to a backside of the holed towel; the separable paper having two holes; and
   an opaque shielding sheet adhered to a front side of the holed towel and between the two holes of the holed towel; and a lower edge of the opaque shielding sheet being adhered upon the holed towel so that the opaque shielding sheet is turnable along the lower edge for shielding one eye of a user;
   wherein the two holes of the separable paper are at positions corresponding to the two holes of the holed towel; when the separable paper is torn, it can be placed upon the face of a user.

2. The eye-surgical holed towel as claimed in claim 1, wherein the shielding sheet has a gluing section, when the separable paper is torn, it can be adhered to an eye of the user.

3. The eye-surgical holed towel as claimed in claim 1, wherein one side of one of the two holes of the holed towel is adhered with a guide bag; an opening of the guide bag is adhered to the holed towel and is corresponding to one hole of the holed towel for collecting undesired objects flowing from the eyes in surgery.

4. The eye-surgical holed towel as claimed in claim 3, wherein a lateral side of the opening of the guide bag is stuck to the front side of the holed towel by gluing.

5. The eye-surgical holed towel as claimed in claim 2, wherein the guide bag is made of PVC.

6. The eye-surgical holed towel as claimed in claim 1, wherein opaque shielding sheet is made of non-weaving cloth.

7. The eye-surgical holed towel as claimed in claim 1, wherein a coverage of the holed towel is sufficient to cove the forehead, jaw, cheek and ears of a user.

8. The eye-surgical holed towel as claimed in claim 1, wherein a folding line is formed at the shielding sheet so as to form a slightly upward-inclined area; wherein by the slightly upward-inclined area of the shielding sheet, the doctor can turn the shielding sheet by fingers.

* * * * *